(12) United States Patent
Lee et al.

(10) Patent No.: US 12,678,327 B2
(45) Date of Patent: Jul. 14, 2026

(54) CAPSULOTOMY DEVICE

(71) Applicant: TI INC., Goyang-si (KR)

(72) Inventors: Hong Jai Lee, Seoul (KR); Sun Joon Hwang, Yongin-si (KR)

(73) Assignee: TI INC., Goyang-si (KR)

( * ) Notice: Subject to any disclaimer, the term of this patent is extended or adjusted under 35 U.S.C. 154(b) by 231 days.

(21) Appl. No.: 18/531,730

(22) Filed: Dec. 7, 2023

(65) Prior Publication Data

US 2024/0099886 A1 Mar. 28, 2024

Related U.S. Application Data

(63) Continuation of application No. PCT/KR2022/008121, filed on Jun. 9, 2022.

(30) Foreign Application Priority Data

Jun. 10, 2021 (KR) ........................ 10-2021-0075295
Apr. 28, 2022 (KR) ........................ 10-2022-0053091

(51) Int. Cl.
*A61F 9/007* (2006.01)
*A61B 18/00* (2006.01)
(Continued)

(52) U.S. Cl.
CPC .. *A61F 9/00754* (2013.01); *A61B 2017/0003* (2013.01); *A61B 2018/00875* (2013.01)

(58) Field of Classification Search
CPC ....... A61F 9/00754; A61B 2018/00601; A61B 2018/00875
See application file for complete search history.

(56) References Cited

U.S. PATENT DOCUMENTS 8,882,757 B2 * 11/2014 Muller ............... A61B 18/1815
606/41
2010/0160907 A1 * 6/2010 Trembly ................ A61B 18/18
606/41
(Continued)

FOREIGN PATENT DOCUMENTS

JP 2007-143878 A 6/2007
JP 2010503477 A 2/2010
(Continued)

*Primary Examiner* — Joseph A Stoklosa
*Assistant Examiner* — Annie L Shoulders
(74) *Attorney, Agent, or Firm* — NKL Law; Jae Youn Kim

(57) ABSTRACT

The present invention provides a lens capsule incision device capable of applying differential power for lens capsule incision to a lens capsule incising part according to the contact states of electrodes of the lens capsule incising part with the lens capsule. The lens capsule incision device, which has a lens capsule incising part adapted to incise the lens capsule and having electrodes, includes: a measuring part for measuring an impedance in a state in which the electrodes of the lens capsule incising part come into contact with the lens capsule; a state determining part for determining a current contact state of the electrodes with the lens capsule, based on the impedance measured through the measuring part; and a power application part for applying differential power for lens capsule incision to the lens capsule incising part according to the current contact state determined by the state determining part.

3 Claims, 8 Drawing Sheets

(51) Int. Cl.
   *A61F 17/00*      (2006.01)
   *A61B 17/00*      (2006.01)

(56)            References Cited

U.S. PATENT DOCUMENTS

| | | | |
|---|---|---|---|
| 2010/0280509 A1* | 11/2010 | Muller | A61B 18/18 |
| | | | 606/33 |
| 2014/0207137 A1* | 7/2014 | Keller | A61F 9/0079 |
| | | | 606/107 |
| 2015/0216442 A1 | 8/2015 | Lavy et al. | |
| 2020/0155348 A1 | 5/2020 | Lee et al. | |
| 2020/0253504 A1 | 8/2020 | Shen et al. | |

FOREIGN PATENT DOCUMENTS

| | | | |
|---|---|---|---|
| JP | 2012-508087 A | 4/2012 |
| JP | 5719022 B2 | 5/2015 |
| KR | 10-2011-0084887 A | 7/2011 |
| KR | 10-1484418 B1 | 1/2015 |
| KR | 10-1863883 B1 | 6/2018 |
| WO | 2021108704 A1 | 6/2021 |

* cited by examiner

CAPSULOTOMY DEVICE

TECHNICAL FIELD

The present invention relates to a lens capsule incision device, more specifically to a lens capsule incision device that is capable of incising the anterior surface of the lens capsule surrounding the lens of the eye.

BACKGROUND ART

The human eyes (eyeballs) are the organs that capture light intensity and wavelength to allow the human to see, and each eye includes the cornea that is a transparent avascular tissue covering the outer surface of the sclera and reflecting light, the lens that is a colorless and transparent organ, serving like a camera lens, the iris that is the colored part making up the eye color and adjusting an amount of light into entering the eye, serving like a camera aperture, and the retina that is a transparent nervous tissue, serving like a camera film.

The lens of the eye corresponds to a camera lens, and if the camera lens becomes dirty, a degree of picture resolution becomes deteriorated badly. Like this, if the lens becomes cloudy, light does not come through the eye well, and accordingly, an object is not seen clearly. A cataract is a clouding of the lens in the eye, which occurs by various causes.

If a cataract occurs, a quick treatment is carried out to prevent the eyesight from getting worse or lost, and a method for treating a cataract, which is widely used, includes the steps of incising the lens capsule surrounding the lens, pulverizing the lens located inside the lens capsule using ultrasound waves, removing the pulverized lens using ultrasound waves, and inserting an artificial lens replacing the removed lens. That is, the sclera or cornea is incised to a width of about 2 to 3 mm with a diamond knife, and then, an incision instrument whose end is bent is inserted into the incised portion to scrape and remove the anterior surface of the lens capsule to a given shape. After that, the exposed lens is pulverized using ultrasound waves, and the pulverized lens is sucked and discharged to the outside. Next, the artificial lens replacing the removed lens is fixedly inserted into the place.

The incision of the lens capsule is an important process determining the safety of cataract surgery, and in the process, a surgeon finely incises the cornea, inserts an incision instrument into the finely incised portion, scrapes the anterior surface of the lens capsule several times using the incision instrument, and exposes the lens to the outside. The fine incision of the cornea should be minimized in width to achieve quick recovery after surgery and eyesight stabilization, and accordingly, the incision instrument requiring excessive incision cannot be used upon real surgery. While the incision instrument is being used to incise the anterior surface of the lens capsule, further, it has to move several times very carefully, thereby making the surgery difficult and causing the surgery time to become long. Accordingly, it is hard to incise the lens capsule to an appropriate size and shape clearly and accurately through the use of the incision instrument, and if the surgeon fails to incise the lens capsule to an appropriate size and shape, radial tear may occur.

Therefore, there is a need to develop a device for incising the lens capsule to the shape of a circle quickly and accurately.

DISCLOSURE OF THE INVENTION

Technical Problems

Accordingly, the present invention has been made in view of the above-mentioned problems occurring in the related art, and it is an object of the present invention to provide a lens capsule incision device that is capable of applying differential power for lens capsule incision to a lens capsule incising part according to the contact states of electrodes of the lens capsule incising part with the lens capsule.

Technical Solutions

To accomplish the above-mentioned objects, according to the present invention, there is provided a lens capsule incision device capable of applying differential power for lens capsule incision to a lens capsule incising part according to the contact states of electrodes of the lens capsule incising part with the lens capsule.

Advantageous Effects of the Invention

According to the present invention, the lens capsule incision device is configured to apply the differential power for lens capsule incision to the lens capsule incising part according to the contact states of the electrodes with the lens capsule, so that the lens capsule incising part makes use of the heat or plasma generated by the current or high frequency power applied according to the contact state between the electrodes thereof and the lens capsule to incise the lens capsule to the shape of the circle quickly and accurately.

BEST MODE FOR INVENTION

Figure 1:
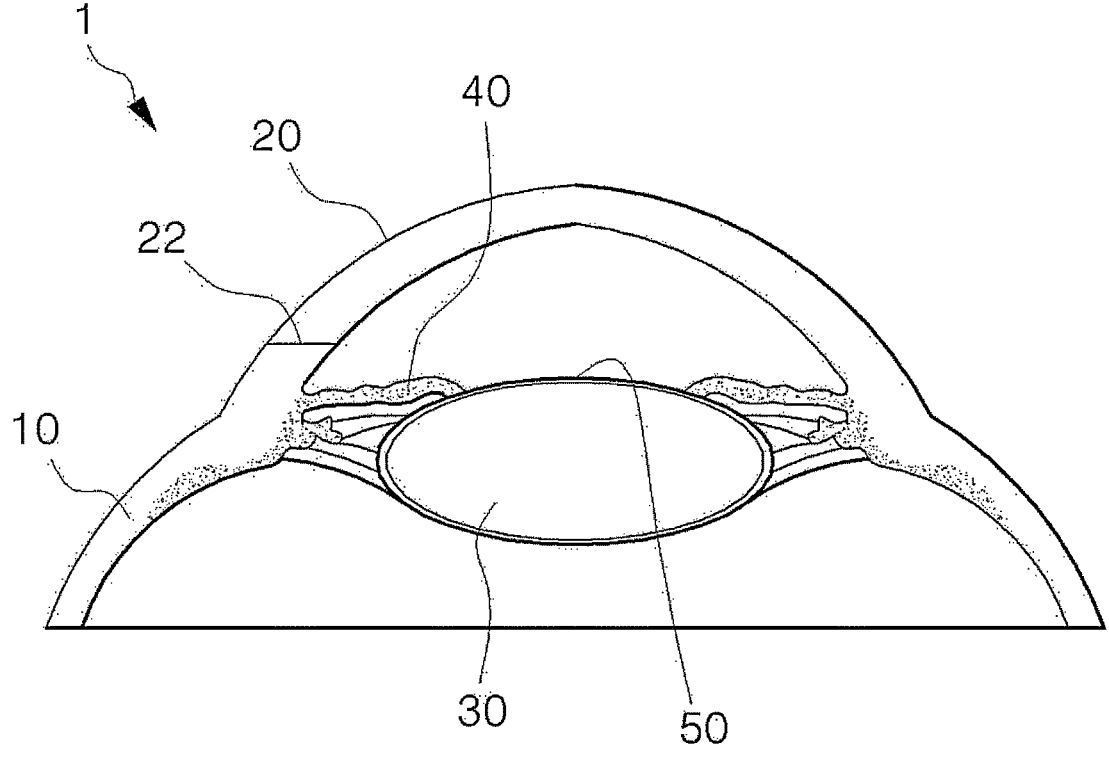
FIG. 1 is a schematic view showing the human eye.

The present invention provides a lens capsule incision device having a lens capsule incising part adapted to incise the lens capsule and having electrodes, including: a measuring part for measuring an impedance in a state in which the electrodes of the lens capsule incising part come into contact with the lens capsule; a state determining part for determining a current contact state of the electrodes with the lens capsule, based on the impedance measured through the measuring part; and a power application part for applying differential power for lens capsule incision to the lens capsule incising part according to the current contact state determined by the state determining part.

MODE FOR INVENTION

The present invention may be modified in various ways and may have several exemplary embodiments. Specific exemplary embodiments of the present invention are illustrated in the drawings and described in detail in the detailed description.

However, this does not limit the invention within specific embodiments and it should be understood that the invention covers all the modifications, equivalents, and replacements within the idea and technical scope of the invention.

Terms used in this application are used to only describe specific exemplary embodiments and are not intended to restrict the present invention. An expression referencing a singular value additionally refers to a corresponding expression of the plural number, unless explicitly limited otherwise by the context. In this application, terms, such as "comprise", or "include", are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, or parts, or combinations thereof.

All terms used herein, including technical or scientific terms, unless otherwise defined, have the same meanings which are typically understood by those having ordinary skill in the art. The terms, such as ones defined in common dictionaries, should be interpreted as having the same meanings as terms in the context of pertinent technology, and should not be interpreted as having ideal or excessively formal meanings unless clearly defined in the specification.

Hereinafter, an embodiment of the present invention will be described in detail below with reference to the accompanying drawings. In order to facilitate the general understanding of the present invention in describing the present invention, through the accompanying drawings, the same reference numerals will be used to describe the same components and an overlapped description of the same components will be omitted.

Figure 2:
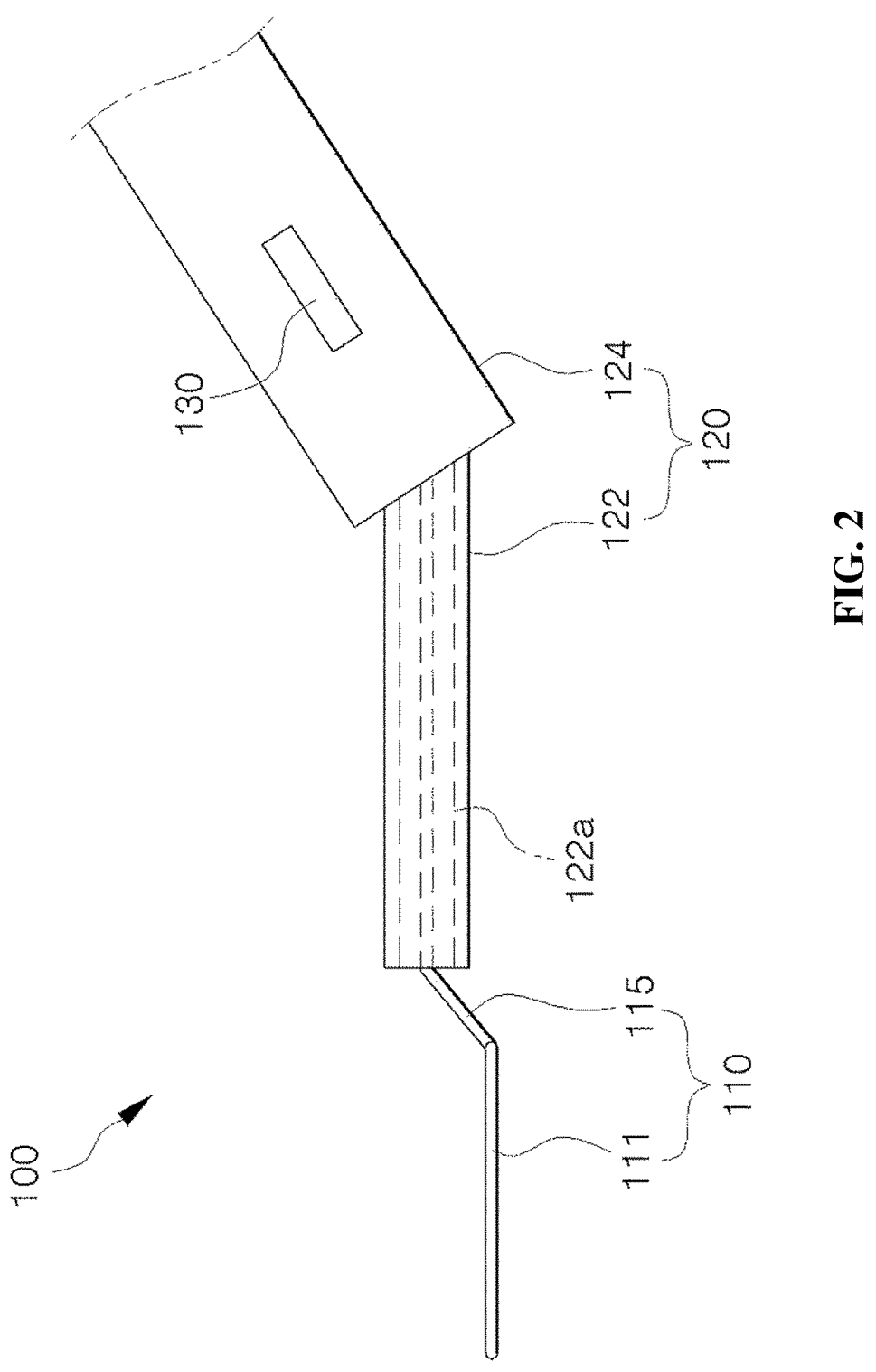
FIG. 2 is a schematic perspective view showing a lens capsule incision device according the present invention.
Figure 3A:
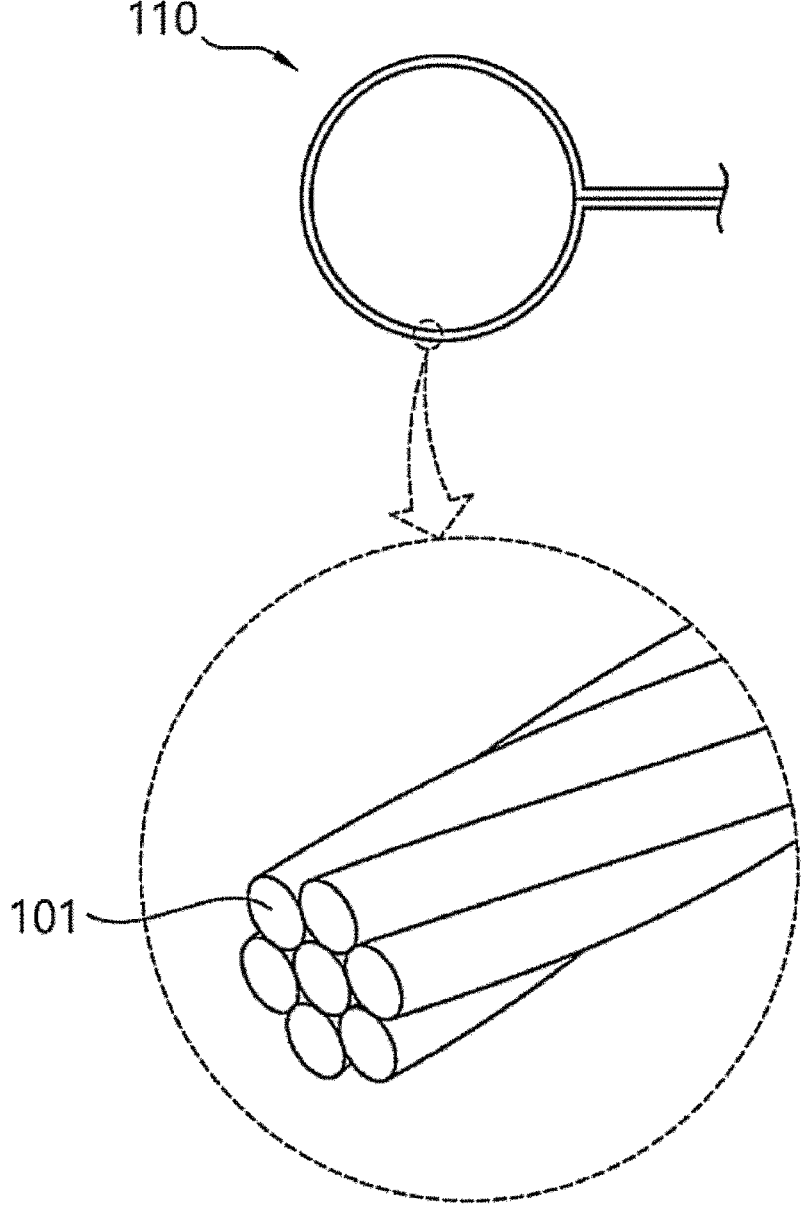
FIG. 3a is an enlarged view showing a lens capsule incising part of the lens capsule incision device FIG. 2.
Figure 3B:
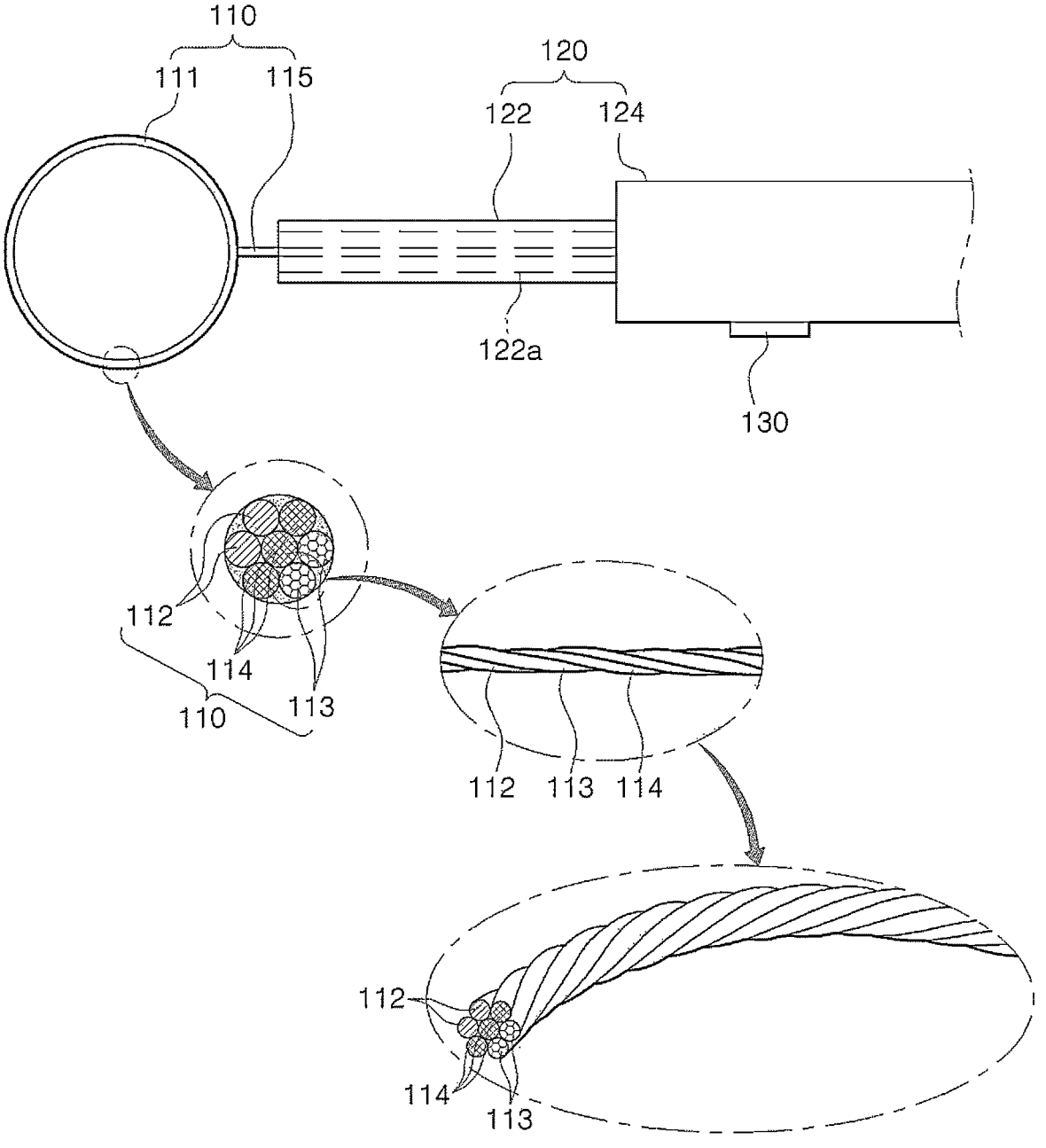
FIG. 3b is an enlarged plan view showing the lens capsule incising part of the lens capsule incision device FIG. 2.
Figure 4:
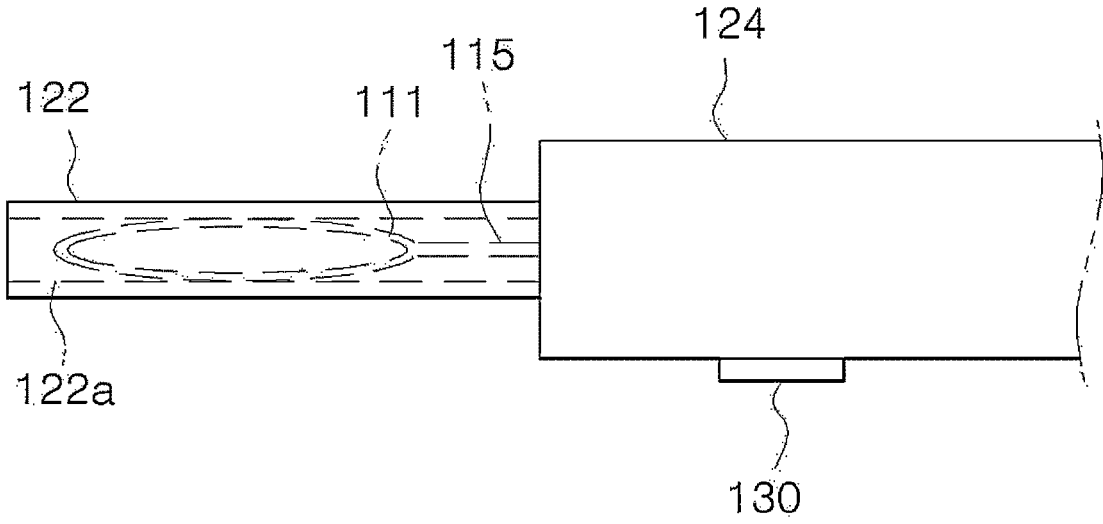
FIG. 4 is a side view showing a state in which the lens capsule incising part of FIG. 2 is inserted into a guide member.
Figure 5:
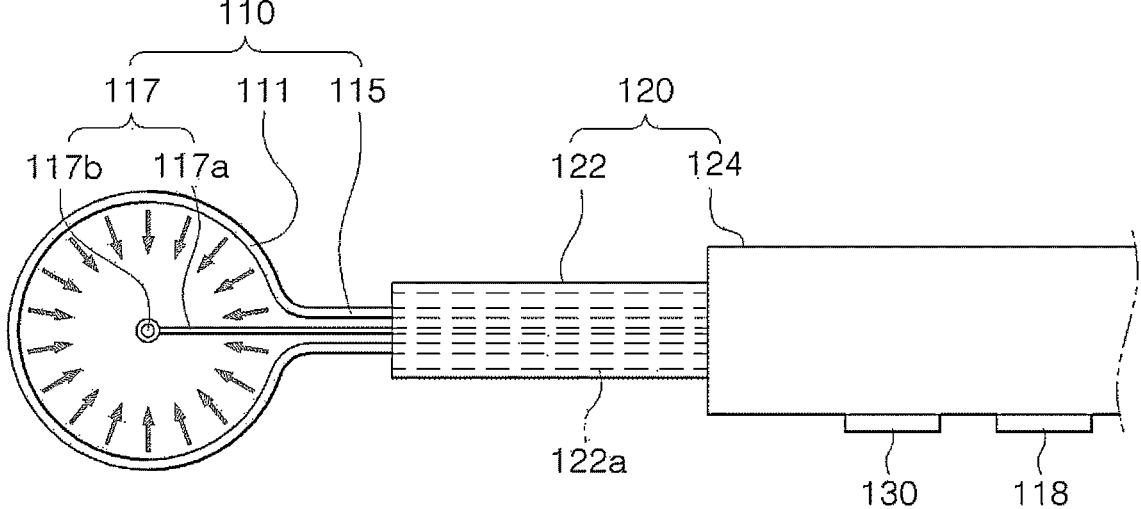
FIG. 5 is a plan view showing another example of the lens capsule incising part of FIG. 2.

FIG. 2 is a schematic perspective view showing a lens capsule incision device according the present invention, FIG. 3 is a plan view showing the lens capsule incision device FIG. 2, FIG. 4 is a side view showing a state in which a lens capsule incising part of FIG. 2 is inserted into a guide member, and FIG. 5 is a plan view showing another example of the lens capsule incising part of FIG. 2.

As shown, a lens capsule incision device 100 according the present invention is configured to be inserted into an incised portion 22 of the cornea 20 or an incised portion (not shown) of the sclera 10 to incise a portion of the lens capsule 50 surrounding the lens 30 to the shape of a circle.

The lens capsule incision device 100 according the present invention largely includes a lens capsule incising part 110, a body part 120, and a button 130.

The lens capsule incising part 110 has the shape of a closed curve and is inserted into the incised portion 22 of the cornea 20 or the incised portion (not shown) of the sclera 10 to incise the lens capsule 50 to the shape of a circle.

Figure 6:
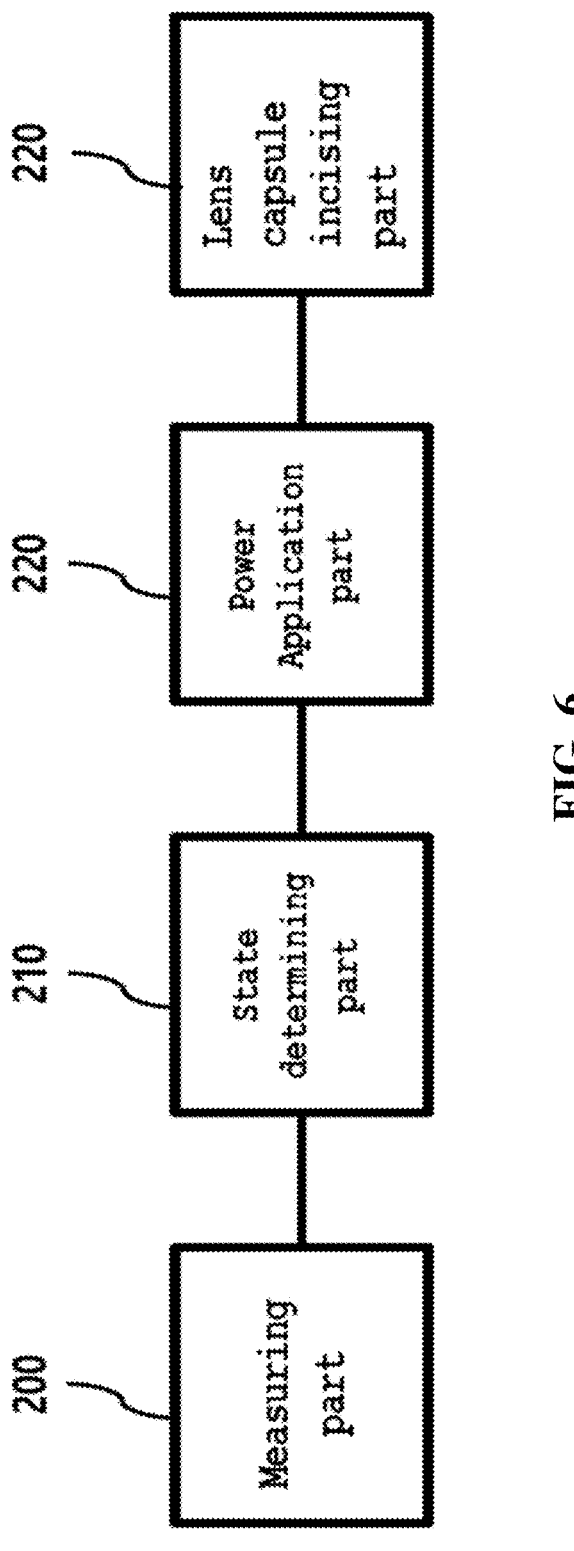
FIG. 6 is a block diagram showing the lens capsule incision device according to the present invention.

That is, the lens capsule incising part 110 makes use of heat or plasma generated by given current or high frequency power for the lens capsule incision applied from a power application part (as shown in FIG. 6) as will be discussed later to heat the water contained in the lens capsule 50 coming into contact therewith within a short time and thus incise the lens capsule 50 to the shape of the circle.

Referring to FIG. 3a, the lens capsule incising part 110 having the shape of a circular loop consists of wire rope with a plurality of metal wires 101 or metal strands twisted around each other. The wire rope has the plurality of strands twisted together, and for example, the wire rope has a rope core located at the center thereof and a plurality of strands twisted around the rope core.

According to an embodiment of the present invention, the lens capsule incising part 110 having the shape of the circular loop is formed of the wire rope having a structure of 1×7, but of course, it may be formed of wire rope having a different structure. Further, each strand consists of wires having the same diameter or different diameters in such a way as to be twisted in a single layer or in multiple layers, and otherwise, each strand may consist of a single wire.

The wire rope with the plurality of conductive metal strands twisted together has better elastic and returning forces than the wire rope with the single wire, and accordingly, the electrodes of the wire rope, which pass through a nozzle type insertion part, are returned excellently to their original shape.

An insulation layer (not shown), which is applied to the periphery of the lens capsule incising part 110, desirably has a color contrasting with the color of the eyeball.

Referring to FIG. 3b, the lens capsule incising part 110 includes a circular incision member 111, a moving member 115, and a current application member (not shown).

In tis case, the circular incision member 111 includes first wires 112 and second wires 113, and it further includes coated wires 114.

The circular incision member 111 serves to incise the lens capsule 50 to the shape of a circle.

The moving member 115 has one end connected to the circular incision member 111 and slidingly moves the circular incision member 111 by the operation of the button 130 as will be discussed later.

The first wires 112 may become active electrodes, and the second wires 113 may become return electrodes.

For example, if current is applied to the lens capsule incising part 110, the current is applied to the first wires 112 through the current application member (not shown), and next, the current applied to the first wires 112 flows to the second wires 113 as the return electrodes.

For example, as shown in FIG. 3a, if the circular incision member 111 consists of only circular wires as active electrodes so that counter electrodes (not shown) are located on a patient's thigh or arm in such a way as to be spaced apart from the wires, the current applied through the wires is applied to the counter electrodes (not shown) through the patient's body, and in this case, the body resistances are different according to individual patients, thereby causing power variations.

To solve such a problem, as shown in FIG. 3b, the circular incision member 111 is configured to have the first wires 112 and the second wires 113 located on both sides of the coated wires 114. The coated wires 114 serve to constantly maintain the resistance values between the first wires 112 and the second wires 113, thereby reducing power variations.

An insulation layer (not shown), which is applied to the periphery of each coated wire 114, desirably has a color contrasting with the color of the eyeball. This enables a surgeon to easily recognize whether the circular incision member 111 inserted into the incised portion 22 of the cornea 20 is accurately located at the center of the anterior surface of the lens capsule 50.

The circular incision member 111 has the first wires 112, the second wires 113, and the coated wires 114 twisted together to the shape of rope, thereby obtaining a big elastic force, and in this case, the first wires 112 and the second wires 113 are desirably made of a metal material with elasticity.

The lens capsule incising part 110 slidingly moves into the body part 120, and if it is desired to incise the lens capsule 50, the lens capsule incising part 110 is exposed to the outside from the body part 120, as shown in FIG. 3b. Contrarily, if it is not desired to incise the lens capsule 50, the lens capsule incising part 110 is inserted into the body part 120, as shown in FIG. 4.

The body part 120 includes a guide member 122 and a body 124.

The guide member 122 serves to allow the lens capsule incising part 110 to slidably move therein and to guide the lens capsule incising part 110 to pass through the incised portion 22 of the cornea 20.

The guide member 122 is made of a silicone material and has a moving hole 122a formed on the central portion thereof to slidingly move the lens capsule incising part 110 therealong.

As the moving hole 122a is formed inside the guide member 122, the lens capsule incising part 110 slidably moves inside the moving hole 122a. In this case, if it is desired to incise the lens capsule 50, the lens capsule incising part 110 is exposed to the outside from the moving hole 122a, and contrarily, if it is not desired to incise the lens capsule 50, the lens capsule incising part 110 is kept inserted into the moving hole 122a.

As mentioned above, the guide member 122 is made of the silicone material, but without being limited thereto, the guide member 122 may be made of others material.

One end of the guide member 133 is connected to the body 24, and the body 123 serves to allow the moving member 115 of the lens capsule incising part 110 to slidably move therein. In this case, the body 124 desirably has a moving hole (not shown) formed therein to slidingly move the moving member 115 therealong.

The guide member 122 is desirably connected slantly to the body 124, and one end of the moving member 115 connected to the circular incision member 111 is desirably formed slantly.

As the guide member 122 and the body 124 are connected slantly to each other and the moving member 115 is formed slantly, the surgeon easily performs the circular incision of the lens capsule 50 using the circular incision member 111 after he or she has inserted the guide member 122 into the incised portion 22 of the cornea 20 or the incised portion (not shown) of the sclera 10.

The button 130 is located on one surface of the body part 120 to slidably move the lens capsule incising part 110 inside the body part 120. As the button 130 is operated by the surgeon, the lens capsule incising part 110 is exposed from the interior of the body part 120 to perform the circular incision of the lens capsule 50 or inserted into the body part 120.

Further, as shown in FIG. 5, the lens capsule incising part 110 further includes a current inducing member 117. Besides, as shown in FIG. 5, the body part 120 further includes a first button 118.

The current inducing member 117 slidably moves so that it is inserted into the body part 120 or exposed to the outside from the body part 120.

The current inducing member 117 is located at the center of the circular incision member 111 when exposed to the outside from the body part 120 and serves to induce the flow of current to the center of the circular incision member 111.

The current inducing member 117 includes a moving bar 117a and a current inducing piece 117b.

The current inducing member 117 slidably moves through the operation of the first button 118 located spaced apart from the button 130 on one surface of the body part 120 so that it is inserted into the body part 120 or exposed to the outside from the body part 120.

One end of the moving bar 117a is connected to the first button 118, and the other end thereof moves to the center of the circular incision member 111 by the operation of the first button 118.

The current inducing piece 117b is formed integrally with the other end of the moving bar 117a.

The current inducing piece 117b serves to induce the flow of current to the circular incision member 111. That is, the current inducing piece 117b induces the current flowing along the circular incision member 111 to the inside of the circular incision member 111, so that the lens capsule incising part 110 easily incises the lens capsule 50 to the shape of the circle.

Figure 7:
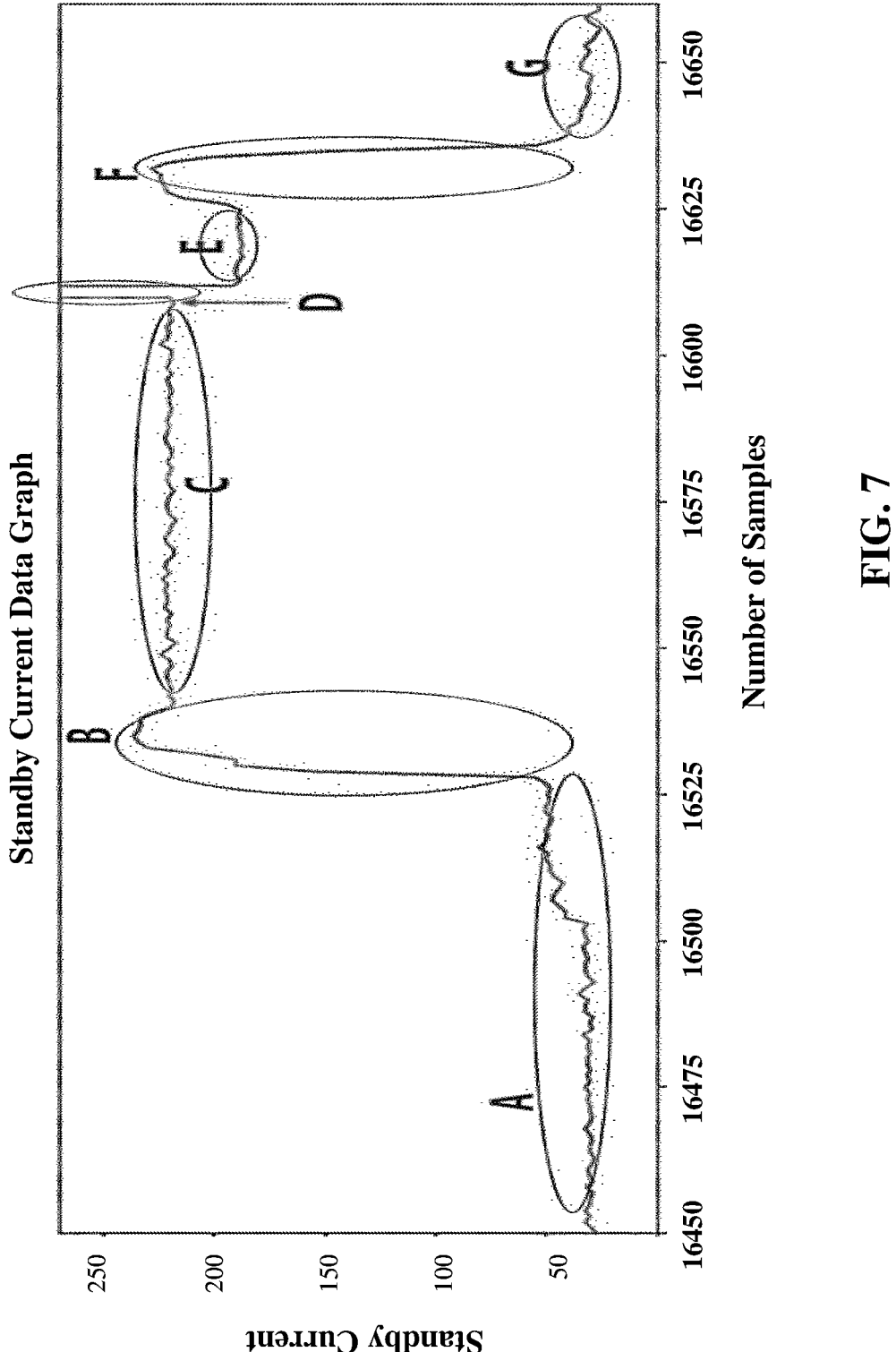
FIG. 7 is a graph adopted to explain a measuring part of FIG. 6.

FIG. 6 is a block diagram showing the lens capsule incision device according to the present invention, and FIG. 7 is a graph adapted to explain a measuring part of FIG. 6.

The present invention is applicable to the lens capsule incision device as shown in FIGS. 1 to 5, and the lens capsule incision device according to the embodiment of the present invention includes a measuring part 200, a state determining part 210, and a power application part 220.

The measuring part 200 measures the impedance of an intraocular tissue (e.g., the lens capsule) in a state in which the lens capsule incising part 110 comes into contact with the intraocular tissue.

That is, the measuring part 200 serves to measure the impedance of the intraocular tissue (e.g., the lens capsule) before the lens capsule 50 is incised. The measuring part 200 applies a given test current to the electrodes of the lens capsule incising part 110 coming into contact with the intraocular tissue (e.g., the lens capsule) every about 100 ms, reads the voltage value corresponding to the test current flowing through the electrodes every application time, and measures the impedance of the intraocular tissue (e.g., the lens capsule) currently coming into contact with the lens capsule incising part 110.

In this case, the electrodes of the lens capsule incising part 110 represent the first wires (active electrodes) and the second wires (return electrodes) of the circular incision member 111. Further, the test current represents the current for incising the lens capsule 50 or the current lower than high frequency power, and accordingly, it can be understood that the test current represents the current capable of measuring impedance.

The measuring part 200 measures about seven impedances as shown in FIG. 7 according to the contact states of the electrodes of the lens capsule incising part 110 with the intraocular tissue (e.g., the lens capsule).

For example, in a state before the electrodes are inserted into the eyeball from the outside of the eyeball, the measuring part 200 measures a first impedance having variations as shown in a portion A of FIG. 7. Further, in a state in which the electrodes are being inserted into the eyeball from the outside of the eyeball, the measuring part 200 measures a second impedance having variations as shown in a portion B of FIG. 7. Furthermore, in a state in which the electrodes normally come into contact with the lens capsule 50 and are thus kept coming into contact therewith, the measuring part 200 measures a third impedance having variations as shown in a portion C of FIG. 7. Besides, in a state in which the electrodes start to output current to the lens capsule 50, the measuring part 200 measures a fourth impedance having variations as shown in a portion D of FIG. 7. Moreover, in a state in which the lens capsule 50 is incised and the electrodes are kept coming into contact with the incised lens capsule 50, the measuring part 200 measures a fifth impedance having variations as shown in a portion E of FIG. 7. Further, in a state in which the electrodes are being removed from the eyeball to the outside, the measuring part 200 measures a sixth impedance having variations as shown in a portion F of FIG. 7. Moreover, in a state in which the electrodes have been removed from the eyeball to the outside, the measuring part 200 measures a seventh impedance having variations as shown in a portion G of FIG. 7.

As mentioned above, the seven contact states of the electrodes of the lens capsule incising part 110 are exemplarily suggested, but the present invention may not be limited thereto.

The state determining part 210 pre-stores impedance information as standard values (or reference values) according to the contact states of the electrodes of the lens capsule incising part 110 with the intraocular tissue (e.g., the lens capsule). For example, the pre-stored impedance information according to the contact states of the electrodes includes at least one or more selected from impedance variation amount, impedance average, impedance distribution, values obtained by analyzing impedance variation amount by convolution, and values calculated through mathematical operations.

For example, the state determining part 210 pre-stores the impedance information as the standard value on the lens capsule 50 for the state before the electrodes are inserted into the eyeball from the outside of the eyeball, the impedance information as the standard value on the lens capsule 50 for the state in which the electrodes are being inserted into the eyeball from the outside of the eyeball, the impedance information as the standard value on the lens capsule 50 for the state in which the electrodes normally come into contact with the lens capsule 50 and are kept coming into contact therewith, the impedance information as the standard value on the lens capsule 50 for the state in which the electrodes start to output current to the lens capsule, the impedance information as the standard value on the lens capsule 50 for the state in which the lens capsule 50 is incised and the electrodes are kept coming into contact therewith, the impedance information as the standard value on the lens capsule 50 for the state in which the electrodes are being removed from the eyeball to the outside, and the impedance information as the standard value on the lens capsule 50 for the state in which the electrodes have been removed from the eyeball to the outside.

The state determining part 210 determines the current contact state of the electrodes with the lens capsule 50, based on the impedance measured through the measuring part 200.

That is, if the state determining part 210 receives the impedance from the measuring part 200, it compares the received impedance with the pre-stored impedance information according to the contact states of the electrodes, detects the impedance information matching with the received impedance, and finally determines the current contact state of the electrodes with the lens capsule 50. In this case, the matching represents that the impedance information is the same as each other and almost close to each other numerically or in pattern (shape).

If necessary, the state determining part 210 further includes an amplifier (not shown) for amplifying the impedance measured through the measuring part 200 to help signal analysis more accurately performed. Like this, if the state determining part 210 has the amplifier, it determines the current contact state of the electrodes with the lens capsule 50 more easily and accurately, based on the impedance amplified through the amplifier.

The power application part 220 regulates the current or high frequency power to be applied to the lens capsule incising part 110 according to the determined contact state through the state determining part 210 and applies the regulated current or high frequency power to the lens capsule incising part 110.

That is, the power application part 220 stores regulation values of the current or high frequency power to be applied to the lens capsule incising part 110 according to different states (e.g., the state before the electrodes are inserted into the eyeball from the outside of the eyeball, the state in which the electrodes are being inserted into the eyeball from the outside of the eyeball, the state in which the electrodes start to output current to the lens capsule, the state in which the lens capsule is incised and the electrodes are kept coming into contact therewith, the state in which the electrodes are being removed from the eyeball to the outside, and the state in which the electrodes have been removed from the eyeball to the outside) with respect to a preset value of the current or high frequency power to be applied to the lens capsule incising part 110 in the state in which the electrodes normally come into contact with the lens capsule and are kept coming into contact therewith.

Accordingly, the power application part 220 applies differential power (that is, adaptively optimized power) for lens capsule incision to the lens capsule incising part 110 according to the current contact state of the electrodes with the lens capsule 50.

For example, if the state determining part 210 determines that the electrodes normally come into contact with the lens capsule and are kept coming into contact therewith, the power application part 220 applies the preset value of the current or high frequency power to the lens capsule incising part 110.

Further, in the case where the state determining part 210 determines that the electrodes do not normally come into contact with the lens capsule, the electrodes are inserted into the eyeball from the outside of the eyeball, or the electrodes are being removed from the eyeball to the outside, the power application part 220 does not apply the current or high frequency power to the lens capsule incising part 110 even if a user executes output order.

Furthermore, in the case where the state determining part 210 determines that the electrodes start to output current to the lens capsule, the power application part 220 checks whether the lens capsule is incised and the electrodes are kept coming into contact therewith, and if it is checked that the incision is not perfect, the power application part 220 additionally applies the preset value of the current or high frequency power of 20 to 50% of the initial output to the lens capsule incising part 110.

If it is assumed that the value of the current or high frequency power to be applied for the lens capsule incision in the state in which the electrodes normally come into contact with the lens capsule and are kept coming into contact therewith is a standard value (or reference value), the current or high frequency power to be applied in different states from the above mentioned state is added or subtracted by given values to and from the standard value.

As mentioned above, the power application part 220 regulates the current or high frequency power to be applied to the lens capsule incising part 110 according to the determined contact state through the state determining part 210 and applies the regulated current or high frequency power to the lens capsule incising part 110. Otherwise, the power application part 220 has preset current or high frequency power to be applied to the lens capsule incising part 110 according to the respective contact states and applies the preset current or high frequency power corresponding to the determined contact state to the lens capsule incising part 110.

That is, the power application part 220 applies different current or high frequency power to the lens capsule incising part 110 according to the respective states including the state before the electrodes are inserted into the eyeball from the outside of the eyeball, the state in which the electrodes are being inserted into the eyeball from the outside of the eyeball, the state in which the electrodes start to output current to the lens capsule 50, the state in which the lens capsule 50 is incised and the electrodes are kept coming into contact therewith, the state in which the electrodes are being removed from the eyeball to the outside, and the state in which the electrodes have been removed from the eyeball to the outside.

Accordingly, the lens capsule incising part 110 makes use of the heat or plasma generated by the current or high frequency power applied thereto according to the contact state between the electrodes thereof and the lens capsule 50 to heat the water contained in the lens capsule 50 and thus incises the lens capsule 50 to the shape of the circle quickly and accurately.

In spite of having the state in which the electrodes do not normally come into contact with the lens capsule 50, however, if the current or high frequency power corresponding to the state in which the electrodes normally come into contact with the lens capsule and are kept coming into contact therewith is unconditionally applied to the lens capsule incising part 110, the lens capsule 50 may be incised slowly and inaccurately. To solve such a problem, according to the embodiment of the present invention, such differential power is applied to the lens capsule incising part 110 according to the contact state between the electrodes of the lens capsule incising part 110 and the lens capsule 50.

According to the embodiment of the present invention, as mentioned above, the differential power is applied to the lens capsule incising part 110 according to the contact state between the electrodes of the lens capsule incising part 110 and the lens capsule 50. Otherwise, the current for the lens capsule incision may not be applied until the contact state between the electrodes of the lens capsule incising part 110 and the lens capsule 50 becomes the state in which the electrodes normally come into contact with the lens capsule 50 and are kept coming into contact therewith, and if the contact state becomes the state in which the electrodes normally come into contact with the lens capsule 50 and are kept coming into contact therewith, the current for the lens capsule incision may be applied to the lens capsule incising part 110.

In the above, the explanation of the embodiment of the present invention has been given for the lens capsule incision device as shown in FIGS. 2 to 5, but it may be given for other lens capsule incision devices that receive current or high frequency power and thus incise the lens capsule.

Figure 8:
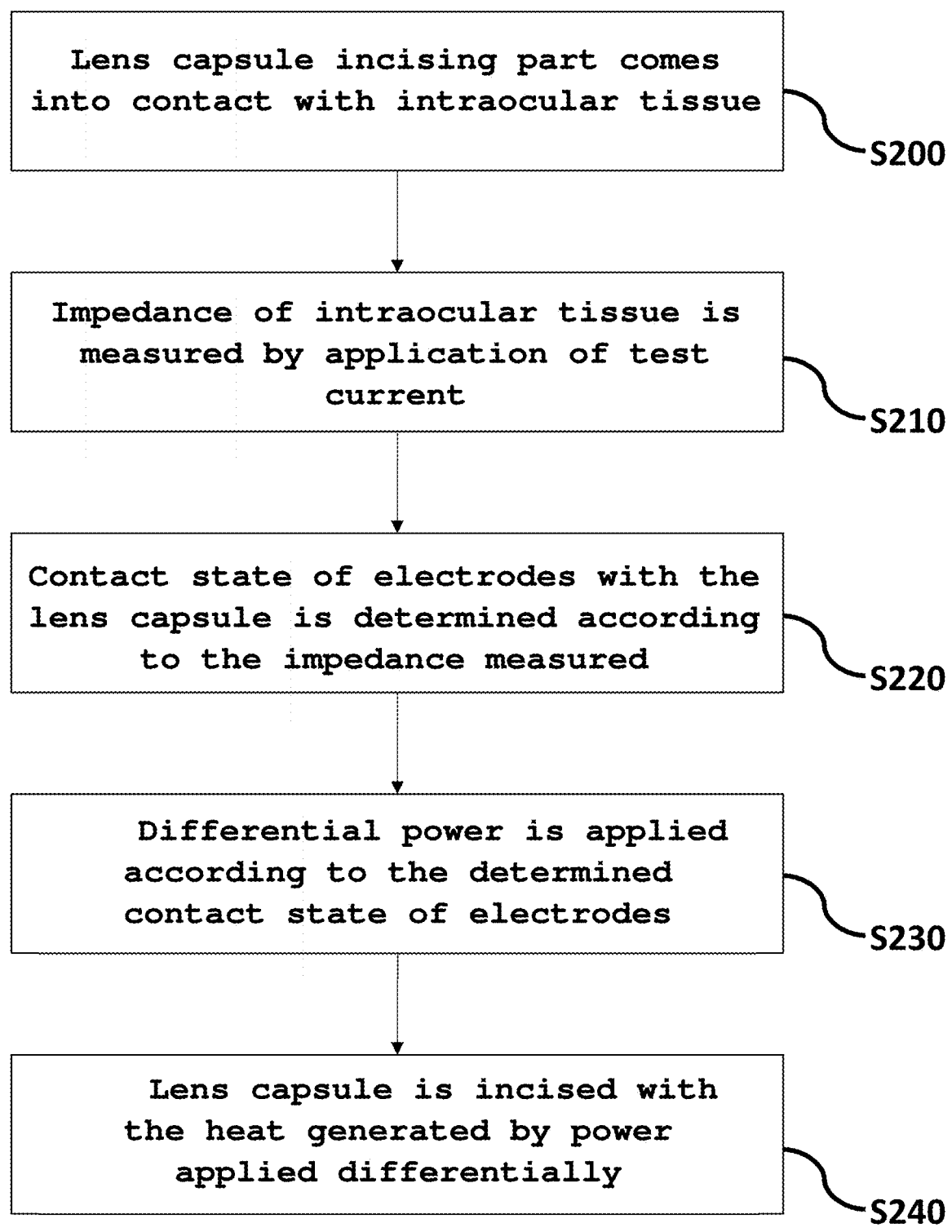
FIG. 8 is a flowchart showing operations of the lens capsule incision device according to the present invention.

FIG. 8 is a flowchart showing operations of the lens capsule incision device according to the present invention.

First, the measuring part 200 measures an impedance of an intraocular tissue (e.g., the lens capsule) in a state in which the lens capsule incising part 110 comes into contact with the intraocular tissue, before the lens capsule 50 is incised (Steps S200 and S210). For example, the surgeon makes the incised portion 22 of the cornea 20 or the sclera 10 using an incision tool and inserts one end of the guide member 122 into the incised portion 22. After that, if the button 130 is operated by the surgeon, the lens capsule incising part 110 is exposed to the outside from the body part 120 and located on top of the lens capsule 50 to be incised. If so, the electrodes (the first wires and the second wires) of the lens capsule incising part 110 come into contact with top of the lens capsule 50. Accordingly, a given test current is applied to the electrodes of the lens capsule incising part 110 coming into contact with the lens capsule 50 every about 100 ms, and the voltage value corresponding to the test current flowing through the electrodes is read every application time to measure the impedance of the intraocular tissue (e.g., the lens capsule) currently coming into contact with the lens capsule incising part 110. For example, the measuring part 200 measures about seven impedances according to the contact states of the electrodes of the lens capsule incising part 110 with the intraocular tissue (e.g., the lens capsule).

Next, the state determining part 210 determines the current contact state of the electrodes with the lens capsule 50, based on the impedance measured through the measuring part 200 (Step S220). That is, if the state determining part 210 receives the impedance from the measuring part 200, it compares the received impedance with the pre-stored impedance information according to the contact states of the electrodes, detects the impedance information matching with the received impedance, and finally determines the current contact state of the electrodes with the lens capsule 50. In this case, the pre-stored impedance information according to the contact states of the electrodes includes at least one or more selected from impedance variation amount, impedance average, impedance distribution, values obtained by analyzing impedance variation amount by convolution, and values calculated through mathematical operations.

After that, the power application part 220 regulates the current or high frequency power to be applied to the lens capsule incising part 110 according to the determined contact state through the state determining part 210 and applies the regulated current or high frequency power to the lens capsule incising part 110 (Step S230). That is, the power application part 220 applies differential power (that is, adaptively optimized power) for lens capsule incision to the lens capsule incising part 110 according to the current contact state of the electrodes with the lens capsule 50.

Next, the lens capsule incising part 110 makes use of the heat or plasma generated by the current or high frequency power applied thereto according to the contact state between the electrodes thereof and the lens capsule 50 to heat the water contained in the lens capsule 50 and thus incises the lens capsule 50 to the shape of the circle quickly and accurately (Step S240).

As mentioned above, the preferred embodiment of the present invention has been disclosed in the specification and drawings. In the description of the present invention, special terms are used not to limit the present invention and the scope of the present invention as defined in claims, but just to explain the present invention. Therefore, persons skilled in the relevant art can appreciate that many modifications and variations are possible in light of the above teachings. It is therefore intended that the scope of the invention be limited not by this detailed description, but rather by the claims appended hereto.

EXPLANATIONS OF REFERENCE NUMERALS

100: Lens capsule incision device
110: Lens capsule incising part
101: Metal wire
111: Circular incision member
112: First wire
113: Second wire
114: Coated wire
115: Moving member
117: Current inducing member
117*a*: Moving bar
117*b*: Current inducing piece
118: First button
120: Body part
122: Guide member
122*a*: Moving hole
124: Body
130: Button
200: Measuring part
210: State determining part
220: Power application part

INDUSTRIAL APPLICABILITY

The lens capsule incision according to the present invention can incise the lens capsule to the shape of a circle quickly and accurately.

The invention claimed is:

1. A lens capsule incision device having a lens capsule incising part configured to incise a lens capsule and having electrodes, comprising:
   a measuring part for measuring an impedance having a different value depending on whether the electrodes of the lens capsule incising part come into contact with the lens capsule;

a state determining part for determining a current contact state of the electrodes with the lens capsule based on the impedance measured by the measuring part, the current contact state corresponding to at least one of contact states associated with the impedance; and
   a power application part for applying differential power for a lens capsule incision to the lens capsule incising part according to the current contact state determined by the state determining part,
   wherein the impedance includes: a first impedance measured before the electrodes are inserted into an eyeball from outside the eyeball; a second impedance measured in a state in which the electrodes are being inserted into the eyeball from outside the eyeball; a third impedance measured in a state in which the electrodes come into contact with the lens capsule and are kept in contact therewith; a fourth impedance measured in a state in which the electrodes start to output current to the lens capsule; a fifth impedance measured in a state in which the lens capsule is incised and the electrodes are kept in contact with the incised lens capsule; a sixth impedance measured in a state in which the electrodes are being removed from the eyeball to the outside; and a seventh impedance measured in a state in which the electrodes are removed from the eyeball to the outside.

2. The lens capsule incision device according to claim 1, wherein the state determining part receives the impedance measured by the measuring part, compares the received impedance with pre-stored impedance information according to the contact states of the electrodes, detects impedance information matching with the received impedance, and determines the current contact state of the electrodes with the lens capsule.

3. The lens capsule incision device according to claim 2, wherein the pre-stored impedance information according to the contact states of the electrodes comprises at least one of an impedance variation amount, an impedance average, an impedance distribution, a value obtained by analyzing the impedance variation amount by convolution, a value calculated through mathematical operations, or any combination thereof.

* * * * *